(12) United States Patent
Toomey

(10) Patent No.: US 6,391,031 B1
(45) Date of Patent: May 21, 2002

(54) DEVICE FOR THE REPAIR OF A HALLUX VALGUS DEFORMITY

(76) Inventor: Eugene P. Toomey, 801 Broadway, Suite 1000, Seattle, WA (US) 98121

( * ) Notice: Subject to any disclaimer, the term of this patent is extended or adjusted under 35 U.S.C. 154(b) by 0 days.

(21) Appl. No.: 09/863,587

(22) Filed: May 17, 2001

(51) Int. Cl.⁷ ................................................ A61B 17/56
(52) U.S. Cl. ............................ 606/87; 606/606; 606/82
(58) Field of Search ............................. 606/87, 88, 89, 606/90, 96, 79, 82

(56) References Cited

U.S. PATENT DOCUMENTS

| 4,565,191 | A |   | 1/1986  | Slocum .................... 128/92 |
| 4,750,481 | A |   | 6/1988  | Reese ...................... 128/92 |
| 5,112,334 | A |   | 5/1992  | Alchermes et al. ........... 606/87 |
| 5,529,075 | A | * | 6/1996  | Clark |
| 5,601,565 | A | * | 2/1997  | Huebner |
| 5,843,085 | A | * | 12/1998 | Graser |
| 6,030,391 | A |   | 2/2000  | Brainard et al. ............. 606/87 |

* cited by examiner

*Primary Examiner*—Pedro Philogene
(74) *Attorney, Agent, or Firm*—Curtis V. Harr

(57) ABSTRACT

A one piece osteotomy guide and method of use, for making a bi plane chevron cut in an osteotomy surgery, such as bunion surgery where accurate redirection of a bone or joint is required. This guide is used to mark a first cut and then placed in the cut. The guide is then used to direct the second cut. Use of the guide allows these cuts to match perfectly, thus speeding the healing process.

18 Claims, 4 Drawing Sheets

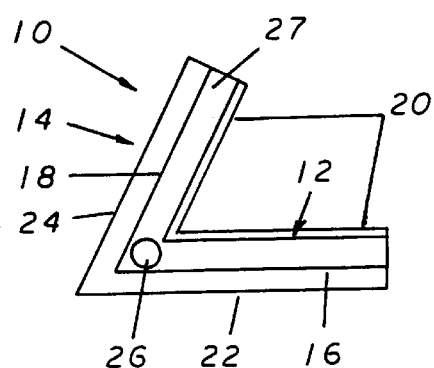
FIG 4
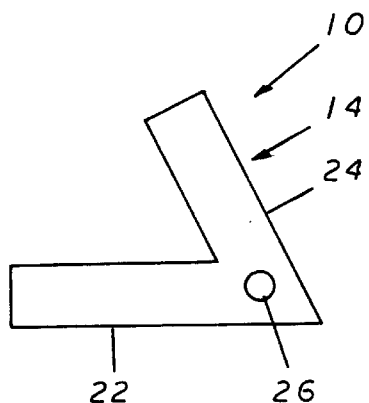
FIG 5
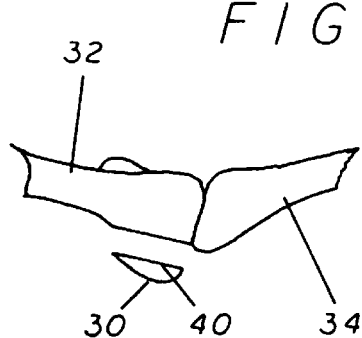
FIG 7
FIG 6
FIG 8

DEVICE FOR THE REPAIR OF A HALLUX VALGUS DEFORMITY

BACKGROUND OF THE INVENTION

The present invention relates to an improvement in the methods used to perform chevron osteotomy procedures that are commonly employed in bunion correction surgery. More specifically, to the design of a device that will aid orthopedic surgeons in making the precise bone cuts that are necessary for the successful completion of a biplane chevron osteotomy procedure and the treatment of a hallux valgus or bunion deformities.

A hallux valgus deformity is a very common foot disorder that results in the formation of a bunion on a patient's foot which can be a source of pain and embarrassment. The deformity is a result of a static subluxation of the first metatarsalphalangeal joint (herein after referred to as the MTP joint) with a lateral deviation of the big toe and a medial deviation of the first metatarsal. More specifically, the word hallux is the medical term for the big toe and valgus is an anatomical term which refers to a deformity that is oriented in a direction away from the midline of the body. That is to say, the term hallux valgus describes a big toe that, from its tip to its base, is deformed in an outward manner in relation to the body of the foot. The condition can also be medically described in terms of the first metatarsal bone as metatarsus primus varus which refers to the orientation of the first metatarsal from its tip to its base being pointed towards the midline of the foot.

The result of this skeletal deformity is very often a large protruding bump on the outside base of the big toe that can be very sensitive to any pressure created by contact. Additionally, the condition is self-perpetuating in that the pressure it creates against the patient's footwear causes the metatarsal bone at the point of contact to thicken. This thickening at the head of the metatarsal increases the size of the resulting bunion which adds to the pressure at the point of contact which in turn increases the severity of the condition and the associated discomfort to the patient.

The most common cause of a hallux valgus condition is the prolonged deformity of a foot which is most commonly associated with the long term wearing of improperly fitting footwear coupled with some sort of preexisting susceptibility resulting from such things as genetic factors or prior trauma. The footwear connection to the disorder is supported by the fact that it is much more common in women who are prone to wearing high heel shoes having a constricted forefoot area. This tends to force the big toe into an abnormal position which can cause the associated muscles to migrate laterally. Once this migration of the muscles passes outside of the line of the MTP joint the resulting hallux valgus condition tends to reenforce itself and continually worsen.

The first step taken in the medical diagnosis and treatment of a hallux valgus condition is to accurately define a number of critical measurements through the use of a series of X-rays taken of the foot's bone structure. One of these is the intermetatarsal angle (herein after referred to as the IM angle) which is defined by the relationship of the first metatarsal shaft compared to the line of the second metatarsal shaft and generally in normal circumstances is between 6 and 9 degrees of deviation.

Another of the measurements taken is the determination of the hallux valgus angle (herein after referred to as the HV angle) which defines the angle of the line created at the MTP joint between the first metatarsal bone shaft and the first phalangeal bone shaft. This angle is generally considered to be within the normal range at 9 to 10 degrees and any HV angle that measures greater than 12 degrees is considered to be in the abnormal range requiring some sort of corrective action to be taken. Additionally, the distal metatarsal articular angle (herein after referred to as the DMAA) can also be measured which quantifies the angle created between the line if the first metatarsal shaft and the metatarsal head's contact surface at the MTP joint.

Finally, the preliminary examination will also include an evaluation of the condition of the MTP joint to determine whether there has been a lateral subluxation of the joint. The combined evaluation of these and other factors will determine the course of action to be taken and in general terms a patient with a congruent MTP joint (a joint with no lateral subluxation), an IM angle of less than 15 degrees, and a HV angle of less than 30 degrees is a candidate for chevron osteotomy corrective surgery. For those patients who's hallux valgus condition does not fall within these parameters there are other corrective procedures available.

The chevron osteotomy procedure for the correction of a hallux valgus condition has been around for a long time so it is quite natural that there exists numerous devices that are intended to aid a surgeon in the performance of a chevron osteotomy. An example of this type of device is illustrated in U.S. Pat. No. 5,843,085 issued to Graser 1998. The Graser patent describes a device which is intended to be used as a cutting guide in three different types of osteotomy procedures and consists of a two piece jig having multiple cutting slots and which may also require the use of more than one KIRSCHNER wire. While the device performs its desired functions, the fact that it is designed to perform multiple functions means that it is inherently complex and cumbersome to use which increases the risks of error when compared to a hypothetical design for a single use device.

Therefor, from the forgoing discussion it can be seen that it would be desirable to provide a device that would aid a surgeon in performing a biplane chevron osteotomy procedure for the correction of a hallux valgus condition. Additionally, that it would be advantageous to provide such a device that would be simple to use and that would allow the surgeon to make the complex bone cuts involved time after time with a high degree of accuracy.

SUMMARY OF THE INVENTION

It is the primary objective of the present invention to provide a means by which a surgeon can use a device that will aid him in making the V-shaped biplane cuts in the first metatarsal bone of a human foot that are necessary to perform a biplane chevron osteotomy procedure to correct a hallux valgus or bunion deformity.

It is an additional objective of the present invention to provide such a device that will allow a surgeon to precisely mark the forward end of the first metatarsal bone in such a manner that will provide a clear guide in making the subsequent primary superior and inferior osteotomy cuts through the stem of the first metatarsal.

It is an additional object of the present invention to provide such a device that will allow for the making of such cuts in the precise location on the metatarsal that is desired and also at the exact 67 degree angle, or formed so as to measure any other angle as desired in the procedure between the superior and inferior components of the primary osteotomy cut in the chevron procedure.

It is an additional objective of the present invention to provide such a device in which the initial marking portion (the primary guide body) is designed in such a way that the forward marking portion will slip into the primary superior and inferior cuts allowing the most forward surface of the secondary guide body to fit tightly against the distal surface of the capital fragment of the metatarsal.

It is a further objective of the present invention to provide such a device that has a secondary guide body formed in a such a manner so that its sides are precisely angled to provide the surgeon with guiding surfaces to aid in the making of the secondary superior and inferior cuts necessary to complete the bone cutting stages of the biplane chevron osteotomy.

It is a still further objective of the present invention to provide such a device to aid a surgeon in the performance of a biplane chevron osteotomy that can be easily manufactured in an inexpensive manner which will facilitate its wide distribution and thus improve the quality of the hallux valgus repair procedures taking place and therefor improve the quality of the patient's life.

These objectives are accomplished by the use of a cutting jig apparatus used in biplane chevron osteotomy surgery for the correction of a hallux valgus (or bunion condition) in which the redirection of the joint between the first metatarsal and the first phalangeal bone is performed. The purpose of the chevron osteotomy is to remove a wedge of bone from the forward portion of the first metatarsal which allows these bones to be realigned in a manner that lessens or completely corrects the patient's hallux valgus deformity.

In the past these cuts were typically made by hand in order that the wedge of bone be removed. The problem with this method is that the procedure requires that two cuts be made at precise angles in order for the remaining bone surfaces to match properly so that the osteotomy will heal adequately. While the first of these cuts is relatively easy to make, the second can be very difficult to make without a precise cutting guide. Therefore, the use of freehand techniques of the past led to problems in the length of time the surgical procedure took and often resulted in and errors made during the cutting process which could lead to healing problems.

The first step in the use of the present invention is to remove the medial eminence from the distal head of the first metatarsal. This procedure removes a significant portion of the protruding bone surface that created the problem and leaves a relatively flat surface to work with. Once this has been completed, a perpendicular KIRSCHNER wire (herein after referred to as a K-wire) is inserted into this surface at the center of the metatarsal head. The K-wire then provides a device which allows the present invention to be precisely positioned on the distal surface of the first metatarsal.

The positioning of the present invention is accomplished by slipping the body of the invention over the K-wire by the use of the K-wire hole that longitudinally spans the length of the secondary guide body of the invention. The use of the K-wire in this function serves two purposes. First, it places the invention in a perpendicular orientation to the surface of the metatarsal from which it can be rotated into the proper orientation for bone marking purposes and second, it serves to hold the invention in place during the metatarsal marking operation ensuring that the primary Chevron cuts will be made properly. It should also be stated that other means of holding the device may be possible.

With the V-shaped cutting edge of the present invention in the proper location, the upper surface of the invention is tapped with a hammer which forces the V-shaped cutting edge into the surface of the metatarsal bone leaving a V-shaped mark opening away from the metatarsal head. This mark is then used as a guide, after the removal of the present invention, by a surgeon for making the primary superior and inferior chevron cuts into the body of the metatarsal. After the completion of these cuts, the most forward portion (or the primary guide body) of the present invention is placed within the gap created by the cuts in a manner that places the forward surface of the secondary guide body against the surface of the metatarsal bone. This allows the surgeon to use the outer surfaces of the secondary guide body as guides to make the secondary superior and inferior chevron cuts at angles that will match up perfectly with surfaces of the primary cuts.

The completion of the secondary cuts separates a wedge of bone from the body of the first metatarsal and the present invention is removed from the cuts. The wedge of bone is then removed which leaves an open V-shaped chevron biplane cut having all of the inside cut edges matching perfectly which allows the stem and capital fragments of the first metatarsal to be inwardly realigned in relation to one another to close the gap created by the removal of the bone wedge. This realignment allows the capital fragment of the first metatarsal to be shifted laterally and oriented out of valgus, thus correcting the abnormal shape in the foot created by the long standing valgus drift due to increased DMAA and thereby alleviating the bunion condition. The stem and capital fragments of the first metatarsal are then generally held in place during the healing process by the use of a pin, screw, or other similar device and the healing of the bone will then allow the patient normal use of the foot.

For a better understanding of the present invention reference should be made to the drawings and the description in which there are illustrated and described preferred embodiments of the present invention.

DESCRIPTION OF THE DRAWINGS

FIG. 4 is a top elevation view of the present invention illustrating the differences in width between the superior and inferior limbs of the invention and also the location of the K-wire hole.

FIG. 5 is a bottom elevation view of the present invention illustrating the bottom of the secondary guide body and the location of the K-wire hole.

FIG. 6 is a top elevation view of the skeletal structure of an abnormal human foot in which the presence of a hallux valgus condition has distorted the orientation between the first metatarsal bone and the rest of the foot.

FIG. 7 is a side elevation view of the first metatarsal and first phalangeal bones of a human foot and illustrates the general location of a medial eminence associated with a hallux valgus condition and the manner in which it is removed from the first metatarsal.

FIG. 8 is side elevation view of the first metatarsal and first phalangeal bones of a human foot and illustrates the manner in which a medial eminence is removed from the forward end of the first metatarsal.

DESCRIPTION OF THE PREFERRED EMBODIMENT

Figure 1:
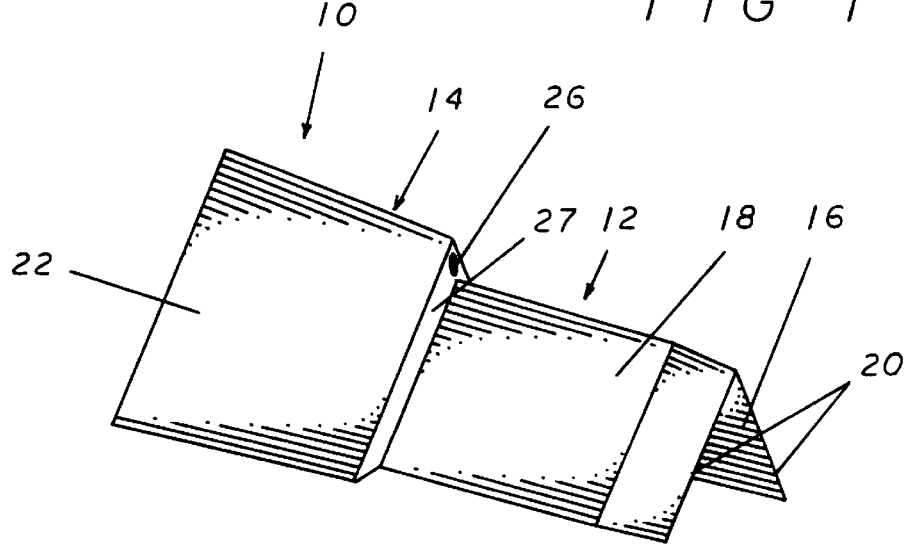
FIG. 1 is a perspective view of the present invention which illustrates the manner in which the primary guide body and the secondary guide bodies are joined together to form the body of the invention.
Figure 2:
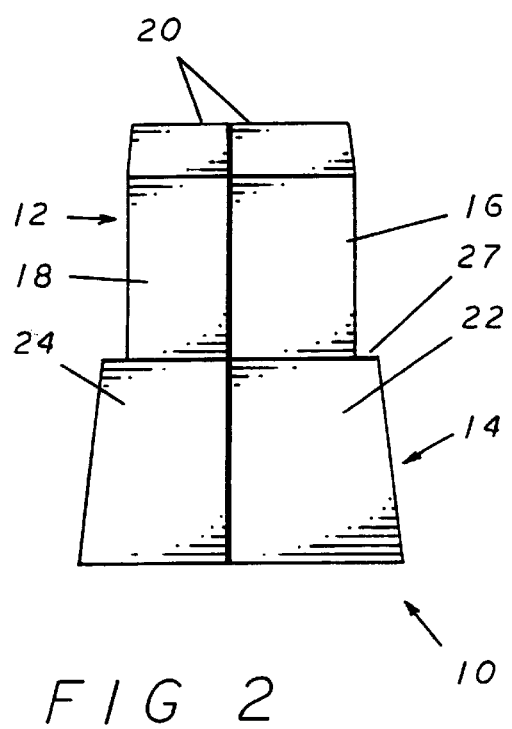
FIG. 2 is a front elevation view of the present invention illustrating the differences in size between the superior and inferior limbs of the invention.
Figure 3:
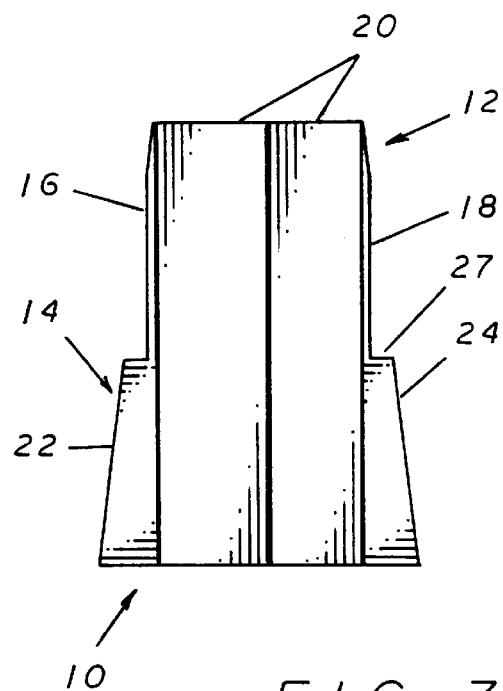
FIG. 3 is a rear elevation view of the present invention illustrating its manner of construction and further detailing the differences in size between the superior and inferior limbs of the invention.

Referring now to the drawings, and more specifically to FIGS. 1, 2, and 3, the chevron osteotomy guide jig 10 is primarily made up of a primary guide body having a sharp leading cutting edge 20 and a secondary guide body 14 which has angled surfaces, in relation to the primary guide body, which are used to guide the orientation and angles of cuts being made during a biplane chevron osteotomy procedure.

The chevron osteotomy guide jig 10 is a relatively small apparatus that is made of a surgical steel or other similar non-corrosive material. It is a generally V-shaped device having two primary components, the primary guide body 12 and the secondary guide body 14, and each of these have two components that make up either side of the V, the superior limb 16 and the inferior limb 18. As their names imply, the superior limb 16 is larger in terms of its span from the central point of the V than the inferior limb 18 is. This difference is due to the invention's use in the biplane chevron osteotomy procedure which in it's preferred embodiment uses an angle for the V of 67 degrees in it's preferred embodiment although other angles may be possible. The combination of the differing lengths of the superior and inferior limbs, 16 and 18, and its V angle produces a device that can exactly reproduce the types of bone cuts that are required in the performance of a biplane chevron osteotomy procedure for the surgical correct of an existing hallux valgus condition. It should also be stated that these lengths may vary as long as they are great enough to span the appropriate bone.

The primary guide body 12 is the component of the present invention which is employed to accurately mark the surface of the appropriate bone in the patient's foot in order to perform the first step of the osteotomy procedure. This marking of the surface of the bone is accomplished by the use of the cutting edge 20 located on the most forward edge of both the superior and limb of the primary guide body 12. The cutting edges 20 are used by precisely placing them against the surface of the bone (a process that will be further discussed below) and tapping the most rearward surface of the invention with a hammer. This imparts exact guide lines into the surface of the bone which the surgeon will follow in making the initial osteotomy cuts.

The secondary guide body 14 is the component of the present invention which is employed by a surgeon to make accurate secondary cuts in the performance of a chevron biplane osteotomy. As with the primary guide body 12, the secondary guide body 14 is V-shaped having two unequal length sides and is located at the most rearward end of the primary guide body 12. The longer, or superior guide surface 22, corresponds in general lateral location in terms of the body of the invention as the superior limb 16 of the primary guide body 12 and likewise, the inferior guide surface 24 correspond to the inferior limb 18 of the primary guide body 12.

The secondary guide body 14 serves as a guide to a surgeon making the secondary cuts in the performance of a biplane chevron osteotomy. In furtherance of this purpose, the walls of the secondary guide body 14 are significantly thicker than those of the primary guide body 12 and the fact that their inner surfaces match perfectly means that the differences in thickness results in an offset that manifests itself on the outer surfaces of the invention. Additionally, the superior and inferior guide surfaces, 22 and 24, of the secondary guide body 14 are angled in such a manner (in relation to the outer surfaces of the primary guide body 12) so as to create a bone cut that angles back toward the first cut. This results in the creation of a excised wedge of bone that can be removed to allow for the realignment of the specific section of bone that is pivotal in a biplane chevron osteotomy procedure. Additionally, the secondary guide body 14 also contains the K-wire hole 26 which passes longitudinally through the secondary guide body 14 just behind the point of the V between the outer surfaces of the primary and secondary guide bodies, 12 and 14. The K-wire hole 26 is the component of the present invention that allows it to be precisely positioned on the surface of the bone prior to the chevron cut marking process.

The manner of construction of the present invention is further illustrated in FIGS. 4 and 5. These FIGS. detail the nature of the secondary guide body 14 and its relationship to the primary guide body 12, the angle of the V-shaped construction of the invention, and the variance in the size of the superior limb 16 in relation to the inferior limb 18. FIG. 4 details the nature of the guide step 27 and the manner in which it provides a gap between the lowest edge of the superior and inferior guide surfaces, 22 and 24, of the secondary guide body 14 and the cutting edge 20 of the primary guide body 12. The guide step 27 and the angled design of the superior and inferior guide surfaces, 22 and 24, function to produce the wedge of bone that is to be removed during the chevron osteotomy procedure as previously described.

These FIGS. also further detail the nature of the V-shaped construction of the present invention highlighting the exact chevron angle created by the V between the superior and inferior limbs, 16 and 18, as well as the difference in length in relation to the point of the V between these components. The precise angle of the body of the invention and the variance of length between the superior and inferior limbs, 16 and 18, are extremely important to the purpose of the present invention as they are both critical to the performance of a proper chevron osteotomy procedure. These FIGS. also further detail the orientation of the K-wire hole 26 in relation to the other components of the invention.

The skeletal structure of an abnormal foot 28 is detailed in FIG. 6 and clearly illustrates the presence of a hallux valgus condition defined by the outwardly protruding MTP joint at the juncture of the first metatarsal 32 and the first phalange bone 34. An additional characteristic of a hallux valgus condition is the presence of a medial eminence 30 which is an outwardly extending bone growth on the medial surface of the most forward end of the first metatarsal 32. The medial eminence 30 is a result of pressure created on the outside edge of the patient's foot which in turn is a result of the outward deviation at the MTP joint.

A hallux valgus condition is clinically diagnosed by taking measurements of certain known bone relationships within a typical human foot. The first of these is known as the hallux valgus angle 66 which defines the relationship between the intersection of the central bone line 82 of the first metatarsal 32 and the central bone line 82 of the first phalange bone 34. More specifically, the HV angle 66 defines the deviation of the central bone line 82 of the first phalange bone 34 from that of the first metatarsal bone 32. An additional measurement that is very often used for diagnostic purposes is the IM angle 78 which defines the relationship between the central bone line 82 of the first metatarsal bone 32 and the central bone line 82 of the second metatarsal 36 and the second phalange bone 38. If the results from either of these measurements are considered to be outside of normal well established parameters one of many available corrective procedures may be indicated of which a chevron osteotomy is one.

The removal of the medial eminence 30 as the first step in a chevron osteotomy procedure is illustrated in FIGS. 7 and 8 which show the placement of the eminence cut 40 in relation to the first metatarsal 32. The removal of the medial eminence 30 at the eminence cut 40 line leaves the flat cut surface 42 on the forward medial surface of the first metatarsal bone 32 which provides a surface upon which the cutting edge 20 of the invention is placed in the preliminary stages of an osteotomy. Additionally, the flat cut surface 42 provides the point of location for the K-wire insertion hole 44 at roughly its center which allows for the perpendicular insertion of the K-wire 46 and therefore, for the precise positioning of the present invention in the marking process.

Figure 9:
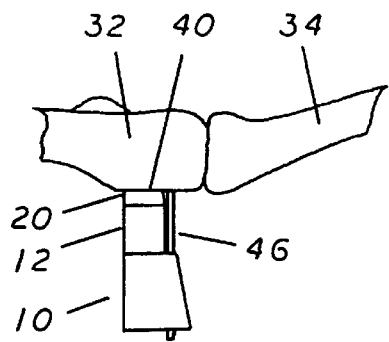
FIG. 9 is a top elevation view of the first metatarsal and first phalangeal bones of a human foot and illustrates the positioning of the present invention in relation to the k-wire that is inserted into the cut portion of the first metatarsal bone.
Figure 10:
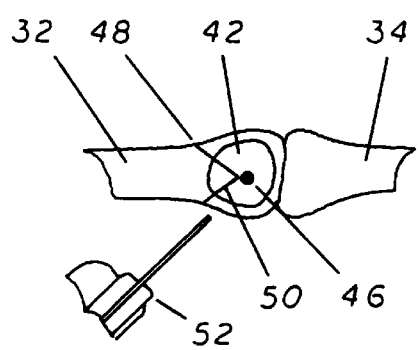
FIG. 10 is a side elevation view of the first metatarsal and first phalangeal bones of a human foot and illustrates the positioning of the cut marks made by the use of the invention that are employed to guide the positioning of the cuts to be made in the first metatarsal bone.

The process by which the present invention is employed to mark the first metatarsal 32 with the superior cut mark 48 and inferior cut mark 50 and the manner in which these marks are used are illustrated in FIGS. 9 and 10. The first step in this process is the placement of the K-wire 46 into the existing K-wire insertion hole 44. This results in a K-wire that extends perpendicularly from the surface of the first metatarsal 32 and provides the structure upon which the present invention is placed in order to obtain the precise positioning required. This is accomplished by orienting the invention so that the primary guide body 12 and cutting edge 20 are pointed towards the medial surface of the first metatarsal 32. From this point, the invention is brought into contact with the bone surface by passing the K-wire 46 through the K-wire hole 26 on the secondary guide body 14. The marking process is then completed by tapping the most rearward surface of the secondary guide body 14 with a surgical hammer. This procedure drives the cutting edge 20 into the surface of the first metatarsal 32 leaving the superior and inferior cut marks, 48 and 50, clearly delineated in the surface of the bone.

Once the marking process has been completed, the present invention is removed from the K-wire 46 giving the surgeon access to the medial surface of the first metatarsal 32. The surgeon is then free to position a surgical saw 52 in line with the superior and inferior cut marks, 48 and 50, from where the preliminary chevron osteotomy cuts can be made. An important feature of the use of the present invention is that the initial marking of the superior and inferior cut marks, 48 and 50, provides for the precise positioning of subsequent cuts that need to be made to complete the osteotomy procedure and to ensure its successful overall outcome.

Figure 11:
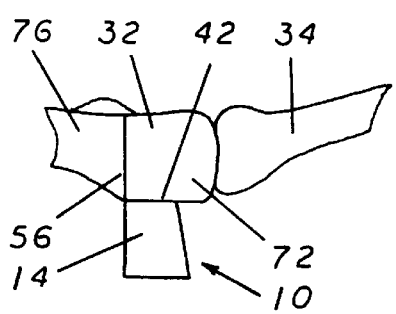
FIG. 11 is a top elevation view of the first metatarsal and first phalangeal bones of a human foot and illustrates the positioning of the present invention with the insertion of the primary guide body within the cuts made where it is again used as a cut guide.
Figure 12:
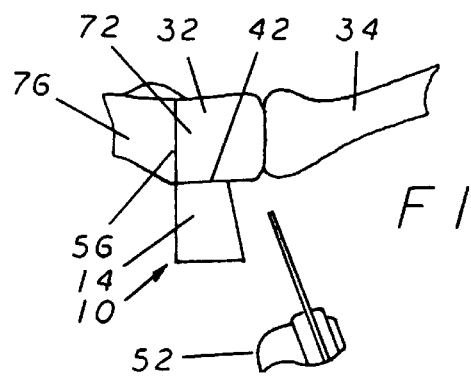
FIG. 12 is a top elevation view of the first metatarsal and first phalangeal bones of a human foot and illustrates the positioning of the present invention when it is being employed as a guide to make the secondary cuts into the surface of the first metatarsal bone.

The execution of the primary superior cut 56 is illustrated in FIGS. 11 and 12 which detail the use of the present invention in the subsequent steps of the chevron osteotomy procedure. It is important to note that these FIGS. do not illustrate the making of or the position of a primary inferior cut, it is none the less inferred to be in an analogous position in reference to the inferior cut mark 50. The result of making these cuts in the first metatarsal 32 is to separate it into the capital fragment 72 which is the portion of the first metatarsal 32 that is forward of the primary superior cut 56 in relation to the foot in general and the medial stem 76 which is the portion of the first metatarsal 32 that is rearward of the primary superior cut 56. Additionally, the cutting process leaves a gap between the capital fragment 72 and the medial stem 76 that corresponds in width to the width of the primary guide body 12 of the present invention.

Once the primary superior cut 56 has been made, the primary guide body 12 component of the present invention is placed within the cuts so that the guide step 27 (not visible in the FIGS.) butts up against the flat cut surface 42 located on the capital fragment 72 of the first metatarsal 32. This placement of the present invention positions the secondary guide body 14 and its associated guide surfaces in a location where the surgeon can use the guide features of the invention to accurately produce the remaining cuts of a biplane chevron osteotomy by again employing the use of the surgical saw 52.

Figure 13:
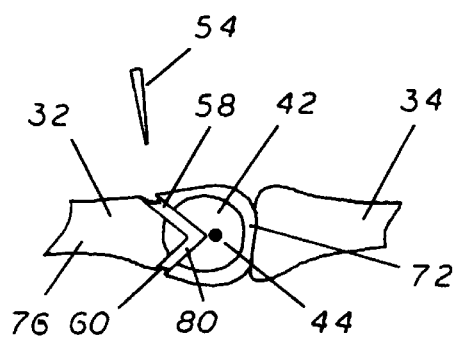
FIG. 13 is a side elevation view of the first metatarsal and first phalangeal bones of a human foot and illustrates the general configuration of a completed cut and the shape of the piece of bone that is removed during a hallux valgus correction procedure.
Figure 14:
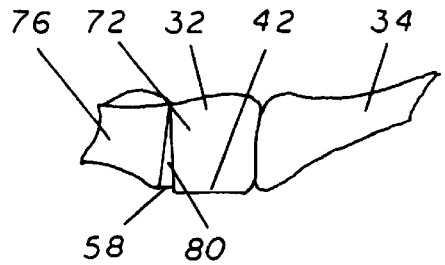
FIG. 14 is a top elevation view of the first metatarsal and first phalangeal bones of a human foot which details the wedge shape of the cut that is made by the use of the present invention in the procedure.

The results of the use of the secondary guide body 14 of the present invention to produce the secondary superior cut 58 and the secondary inferior cut 60 are illustrated in FIGS. 13 and 14. These FIGS. detail both the nature of the bone wedge 54 that is removed from the first metatarsal 32 and the resulting wedge-shaped gap 80 left by the completion of the secondary superior and inferior cuts, 58 and 60, through the body of the first metatarsal 32. The resulting wedge-shaped gap 80 is critical to the completion of a biplane chevron osteotomy as it allows the first metatarsal 32 to be realigned in a manner that provides for the correction of the existing hallux valgus and DMAA condition. More specifically, the realignment of the capital fragment 72 and the medial stem 76 of the first metatarsal 32 results in a lessening of the severe angles created between the joint surface of the first metatarsal 32 and the first metatarsal shaft that characterize the existence of a bunion disorder.

Figure 15:
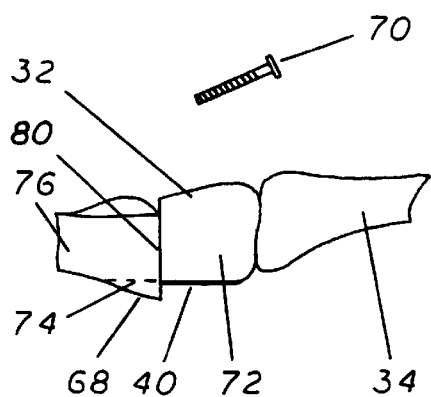
FIG. 15 is a top elevation view of the first metatarsal and first phalangeal bones of a human foot which details the offset of the capital fragment after relocation to correct the hallux valgus condition.
Figure 16:
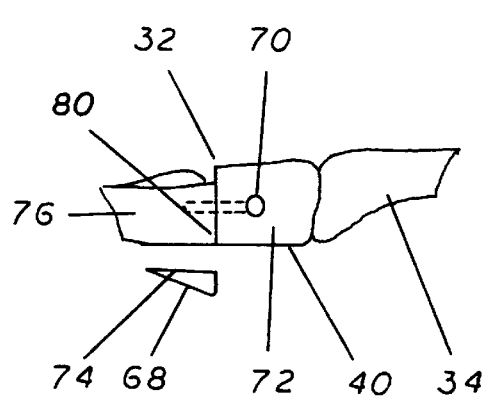
FIG. 16 is a top elevation view of the first metatarsal and first phalangeal bones of a human foot which details the manner in which the bone shelf is removed from the first metatarsal to complete the chevron osteotomy procedure.

The final stages of a chevron osteotomy procedure are illustrated in FIGS. 15 and 16 in which the realignment of the capital fragment 72 and the medial stem 76 of the first metatarsal is detailed. The closing of the wedge-shaped gap 80 causes the capital fragment 72 and the medial stem 76 to be offset in relation to one another resulting in an outwardly extending protrusion of the most forward end of the medial stem 76 known as the medial shelf 68. It is necessary to remove this medial shelf 68 which is done by using a surgical saw 52 to make a shelf cut 74 at a location so as to provide a uniform medial edge at the junction of the capital fragment 72 and the medial stem 76. Additionally, the osteotomy procedure is often accompanied by the use of a stabilizing device such as a fixating screw 70 or other similar bio-compatible apparatus to hold the capital fragment 72 and the medial stem 76 in a constant position during the healing process. Once the healing process is completed the fixating screw 70 can either be removed or left within the repair in compliance with the state of the medical art.

Figure 17:
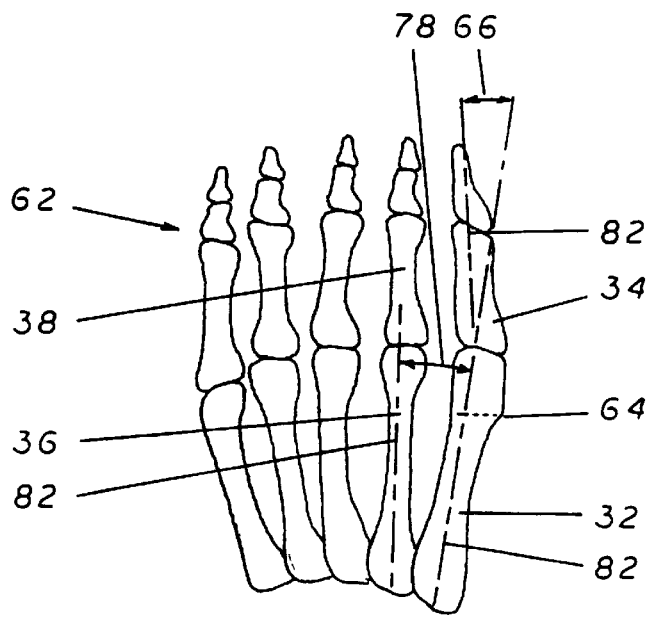
FIG. 17 is a top elevation view of the skeletal structure of the human foot of FIG. 6 and illustrates the relative positions of the first metatarsal and phalangeal bones after the surgical correction has occurred.

Finally, the resulting skeletal structure of a corrected foot 62 is illustrated in FIG. 17 detailing the orientation of the closed bone scar 64 in relation to the rest of the foot. More specifically, this FIG. details the manner in which the central bone lines 82 that define the HV angle 66 and the IM angle 78 have dramatically improved after the completion of a chevron osteotomy procedure when compared to similar measurements previously illustrated in FIG. 6. The result is either the elimination of or the dramatic reduction of the hallux valgus condition which will have the effect of improving the patient's life both physically and emotionally.

Although the present invention has been described in considerable detail with reference to certain preferred versions thereof, other versions are possible. Therefore, the spirit and scope of the appended claims should not be limited to the description of the preferred versions contained herein.

What is claimed is:

1. An osteotomy guide comprising:
   a primary guide body having an upper and lower portion said primary guide body forming a superior and inferior limb each having a superior and inferior guide surface; and
   a secondary guide body having an upper and lower portion, said lower portion fixedly attached to said upper portion of said primary guide, said secondary guide body forming a superior and inferior limb each having a superior and inferior guide surface running nonparallel to said superior and inferior guide surfaces of said primary guide body.

2. An osteotomy guide as in claim 1 further comprising a cutting edge formed on the lower portion of said primary guide body.

3. An osteotomy guide as in claim 2 wherein said secondary guide body forms a k-wire reception hole.

4. An osteotomy guide as in claim 3, wherein said superior and inferior limbs of said primary and secondary guides are connected at a central point and said superior and inferior limbs are angled away from said central point so as to form a V Shape.

5. An osteotomy guide as in claim 4, wherein said primary and secondary limbs and surfaces of said primary and secondary guide bodies have corresponding length sides, said superior limbs and surfaces having longer sides than said inferior limbs and surfaces.

6. An osteotomy guide as in claim 5, wherein the angle formed by said primary and secondary guides and said central point is 67 degrees.

7. An osteotomy guide as in claim 6, wherein said secondary guide body is of a thickness greater than the thickness of said primary guide body.

8. An osteotomy guide as in claim 7, wherein said front of said secondary guide body terminates in a stepped portion.

9. A biplane chevron osteotomy guide comprising:
   a primary guide body having an upper and lower portion said primary guide body forming a superior and inferior limb each having a superior and inferior guide surface;
   a secondary guide body having an upper and lower portion, said lower portion fixedly attached to said upper portion of said primary guide, said secondary guide body forming a superior and inferior limb each having a superior and inferior guide surface running nonparallel to said superior and inferior guide surfaces of said primary guide body; and
   a central point where said superior and inferior limbs of said primary and secondary guides are connected and angled away from said central point so as to form a V Shape.

10. A biplane chevron osteotomy guide as in claim 9 further comprising a cutting edge formed on the lower portion of said primary guide body.

11. A biplane chevron osteotomy guide as in claim 10 wherein said secondary guide body forms a k-wire reception hole.

12. A biplane chevron osteotomy guide as in claim 11, wherein said primary and secondary limbs and surfaces of said primary and secondary guide bodies have corresponding length sides, said superior limbs and surfaces having longer sides than said inferior limbs and surfaces.

13. A biplane chevron osteotomy guide as in claim 12, wherein the angle formed by said primary and secondary guides and said central point is 67 degrees.

14. An osteotomy guide as in claim 13, wherein said secondary guide body is of a thickness greater than the thickness of said primary guide body.

15. An osteotomy guide as in claim 14, wherein said front of said secondary guide body terminates in a stepped portion.

16. A method of performing a biplane chevron osteotomy comprising the steps of:
   incising the layer of skin medial to the first metatarsal head of a hallux valgus deformity, to expose said first metatarsal head;
   removing the medial eminence of the distal head of the first metatarsal head;
   positioning an osteotomy guide having a primary guide body with a first edge and a secondary guide body at a proper location for cutting said first metatarsal;
   tapping said rear secondary guide body with a tapping means, forcing said primary guide body into said first metatarsal head so as to make a mark for cutting;
   cutting a first chevron cut with a cutting means into said first metatarsal along said mark;
   inserting said front of said primary guide body into said first chevron cut until said secondary guide body resides against said first metatarsal;
   cutting with a cutting means a second chevron cut into said first metatarsal along the outer surface of said secondary guide body;
   removing said guide;
   removing a bone wedge created by said primary and secondary cuts, creating a gap at the medial stem and capital fragment of said first metatarsal head;
   realigning said medial stem and capital fragment of said first metatarsal head;
   stabilizing said medial stem to said capital fragment of said first metatarsal head; and suturing said layer of skin exposing said fixated medial stem and capital fragment of said first metatarsal head.

17. A method of performing a biplane chevron osteotomy as in claim 16, wherein stabilizing said medial stem to said capital fragment of said first metatarsal head is preformed using a screw.

18. A method of performing a biplane chevron osteotomy as in claim 17, wherein stabilizing said medial stem to said capital fragment of said first metatarsal head is preformed using a pin.

* * * * *